United States Patent [19]

Deweerdt et al.

[11] Patent Number: 5,198,573
[45] Date of Patent: Mar. 30, 1993

[54] DIESTERS OF HEXENE-1,6-DIOIC ACIDS PRODUCED FROM 1,2-DIALKOXY-3-BUTENES/CO

[75] Inventors: Helene Deweerdt, Lyon; Jean Jenck, Chassieu; Philippe Kalck, Castanet Tolosane; Sylvain Mutez, Irigny; Robert Perron, Charly, all of France

[73] Assignee: Rhone-Poulenc Chimie, Courbevoie, France

[21] Appl. No.: 762,402

[22] Filed: Sep. 19, 1991

[30] Foreign Application Priority Data

Sep. 24, 1990 [FR] France ................... 90 12042

[51] Int. Cl.⁵ ............................... C07C 67/37
[52] U.S. Cl. ..................... 560/204; 560/190; 562/550; 562/595
[58] Field of Search ............... 560/204, 190; 562/550, 562/595

[56] References Cited

U.S. PATENT DOCUMENTS

4,611,082  9/1986  Chan et al. .................. 560/204
4,925,973  3/1990  Deweerdt et al. ............ 560/204

FOREIGN PATENT DOCUMENTS

0217407  8/1987  European Pat. Off. .
0347340  12/1989  European Pat. Off. .

*Primary Examiner*—Jose G. Dees
*Assistant Examiner*—Vera C. Clarke
*Attorney, Agent, or Firm*—Burns, Doane, Swecker & Mathis

[57] ABSTRACT

Diesters of hexene-1,6-dioic acids are prepared by reacting at least one 1,2-dialkoxy-3-butene with carbon monoxide in the presence of a catalytically effective amount of a palladium-based catalyst and a halogen compound, in liquid phase, at elevated temperature and at superatmospheric pressure.

21 Claims, No Drawings

DIESTERS OF HEXENE-1,6-DIOIC ACIDS PRODUCED FROM 1,2-DIALKOXY-3-BUTENES/CO

BACKGROUND OF THE INVENTION

1. Field of the Invention

The present invention relates to the preparation of diesters of hexene-1,6-dioic acids. Such diesters can be facilely hydrogenated into the corresponding diesters of adipic acid, or adipates, which can in turn be hydrolyzed to form adipic acid. Adipic acid, one of the raw materials for nylon 66, is currently produced in vast amounts and, because of this fact alone, any novel synthesis for this diacid and/or derivatives thereof would be of fundamental interest.

The present invention especially relates to the preparation of diesters of 3-hexene-1,6-dioic acid by reacting carbon monoxides with at least one 1,2-dialkoxy-3-butene in the presence of a palladium-based catalyst.

2. Description of the Prior Art

It is known to this art, per Imamura and Tsuji, Tetrahedron. vol. 25, p. 4187–4195 (1969), to prepare diesters of 3-hexene-1,6-dioic acid by reacting carbon monoxide with 1,4-diethoxy-2-butene in ethanol, in the presence of palladium and chloride.

1,2-Diethoxy-3-butene is mentioned as a coproduct, assumed to originate by an allyl rearrangement of 1,4-diethoxy-2-butene.

U.S. Pat. No. 4,611,082 describes dicarbonylating a 1,4-dialkoxy-2-butene in a polar, aprotic and nonbasic solvent, at 80° to 140° C. in the presence of a transition metal halide, palladium chloride being the most effective.

This same type of reaction, starting with 1,4-dimethoxy-2-butene, is described in detail in *Journal of Molecular Catalysis*, 53. pp. 417–432 (1989).

Over the course of research by the assignee hereof relating to the preparation of dialkoxybutenes from 1,3-butadiene, it has been shown that, in general, a mixture is produced containing especially the 1,4-dialkoxy-2-butene (predominant ether) and the 1,4-dialkoxy-3-butene, these two diethers being relatively difficult to separate from each other.

SUMMARY OF THE INVENTION

A major object of the present invention is the provision of a novel process for the preparation of diesters of 3-hexene-1,6-dioic acid, comprising reacting carbon monoxide with at least one 1,2-dialkoxy-3-butene in the presence of a palladium-based catalyst.

Briefly, the present invention features a process for the preparation of diesters of 3-hexene-1,6-dioic acid, which comprises reacting carbon monoxide with at least one dialkoxybutene in the presence of a palladium-based catalyst and of a halogen compound, in liquid phase, at elevated temperature and at a pressure greater than atmospheric pressure, said at least one dialkoxybutene comprising a 1,2-dialkoxy-3-butene.

DETAILED DESCRIPTION OF THE PREFERRED EMBODIMENTS OF THE INVENTION

More particularly according to the present invention, by "1,2-dialkoxy-3-butene" is intended a 3-butene disubstituted in positions 1 and 2 by identical or different, linear, branched or cyclic alkoxy groups and having from 1 to 12 carbon atoms. The two alkoxy groups are preferably identical and advantageously have from 1 to 4 carbon atoms. 1,2-Dimethoxy-3-butene and 1,2-diethoxy-3-butene are starting materials which are particularly preferred according to the present invention.

In an advantageous embodiment of the process of the invention, the 1,2-dialkoxy-3-butene(s) is (are) used in the form of a mixture with the 1,4-dialkoxy-2-butene(s), in which they may represent a variable molar fraction, for example from 5% to 99% of the said mixture.

Indeed, it has now surprisingly been found that the selectivity for the desired linear diester (linear dicarbonylated product), when starting with such branched diethers (1,2-dialkoxy-3-butene), whether employed alone or mixed with the corresponding linear diethers, is sufficiently high that the starting material may be a mixture of the branched diether and the linear diether in the proportions in which they are present during the stage of their preparation from 1,3-butadiene.

The process according to the present invention is carried out in the presence of a catalytically effective amount of a palladium-based catalyst.

Although the precise mechanism of the catalytically active species in the subject reaction is not completely known, the various palladium compounds and metallic palladium are assumed to be useful precursors in carrying out the process of the invention.

Exemplary palladium sources for carrying out the process of the invention include:

(i) metallic palladium, deposited, if appropriate, on a support substrate such as charcoal, alumina or silica;

(ii) PdCl$_2$, Pd(OAc)$_2$;

(iii) palladium salts or $\pi$-allyl complexes in which the anion coordinated to the Pd cation is selected from among the following anions: carboxylates such as formate, acetate, propionate, benzoate, acetylacetonate, halides such as Cl$^-$ and Br$^-$ and preferably Cl$^-$.

Palladium chloride is advantageously used.

The precise amount of catalyst to be used, which may vary over wide limits, will primarily depend on a compromise between the desired efficiency and the expenditure of catalyst, and the other reaction conditions. In general, good results are obtained using a palladium concentration in the reaction mixture ranging from $10^{-3}$ to 1 mol/l. Below $10^{-3}$ mol/l the kinetics of the reaction are greatly diminished. Amounts of palladium which are greater than 1 mol/l are inconvenient simply from the viewpoint of economy. This concentration preferably ranges from $10^{-2}$ to 1 mol/l.

The process according to the present invention is also carried out in the presence of a halogen compound. Advantageously, an ionic chloride is used in which the cation is selected from among:

(a) alkali metal cations, (b) alkaline earth metal cations, and (c) quaternary onium cations of a Group VB element of the Periodic Table selected from nitrogen and phosphorus, said element being tetracoordinated to carbon atoms, with the proviso that the nitrogen may be coordinated to two pentavalent phosphorus atoms.

Also advantageously, the quaternary onium chloride will comprise a quaternary onium cation corresponding to one of the following formulae (I) to (V):

-continued

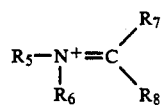
(II)

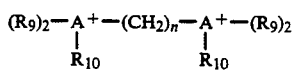
(III)

(IV)

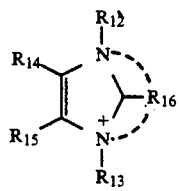
(V)

in which A is a nitrogen or phosphorus atom; $R_1$, $R_2$, $R_3$, $R_4$, which may be identical or different, are each a linear or branched alkyl radical having from 1 to 16 carbon atoms, optionally substituted by a phenyl, hydroxyl, halo, nitro, alkoxy or alkoxycarbonyl group; a linear or branched alkenyl radical having from 2 to 12 carbon atoms, preferably from 4 to 8 carbon atoms, an aryl radical having from 6 to 10 carbon atoms, optionally substituted by one or more alkyl radicals having from 1 to 4 carbon atoms, alkoxy, alkoxycarbonyl or halo radicals, with the proviso that two of said radicals $R_1$ to $R_4$ may together form a linear or branched alkylene, alkenylene or alkadienylene radical having from 3 to 6 carbon atoms; $R_5$, $R_6$, $R_7$, $R_8$, which may be identical or different, are each a linear or branched alkyl radical having from 1 to 4 carbon atoms, with the proviso that the radicals $R_7$ and $R_8$ may together form an alkylene radical having from 3 to 6 carbon atoms, and with the further proviso that the radicals $R_6$ and $R_7$ or $R_6$ and $R_8$ may together form an alkylene, alkenylene or alkadienylene radical having 4 carbon atoms and constituting a nitrogenous heterocyclic ring with N; $R_9$ is a linear or branched alkyl radical having from 1 to 4 carbon atoms or a phenyl radical; $R_{10}$ is a linear or branched alkyl radical having from 1 to 4 carbon atoms, the same as or different from $R_9$, a linear or branched alkenyl radical having from 2 to 12 carbon atoms, preferably from 4 to 8 carbon atoms; n is an integer greater than or equal to 1 and less than or equal to 10 and preferably less than or equal to 6; $R_{11}$ is an aryl radical having from 6 to 10 carbon atoms, optionally substituted by one or more alkyl groups having from 1 to 4 carbons, alkoxy, alkoxycarbonyl or halo groups; $R_{12}$ and $R_{13}$, which may be identical or different, have the definitions given above for $R_1$ to $R_4$; and $R_{14}$ to $R_{16}$, which may be identical or different, are each a hydrogen atom, a linear or branched alkyl radical having from 1 to 16 carbon atoms, optionally substituted by a phenyl, hydroxyl, halo, nitro, alkoxy or alkoxycarbonyl group, a linear or branched alkenyl radical having from 2 to 12 carbon atoms, preferably from 4 to 8 carbon atoms, an aryl radical having from 6 to 10 carbon atoms, optionally substituted by one or more alkyl radicals having from 1 to 4 carbon atoms, alkoxy, alkoxycarbonyl or halo radicals, with the proviso that the radicals $R_{14}$ and $R_{15}$ may together form a linear or branched alkylene, alkenylene or alkadienylene radical having from 3 to 6 carbon atoms, to constitute an aromatic ring with the two adjoining carbon atoms of the imidazole ring.

The following cations are exemplary quaternary onium cations corresponding to the formula I: Tetramethylammonium, Triethylmethylammonium, Tributylmethylammonium, Trimethyl(n-propyl)ammonium, Tetraethylammonium, Tetrabutylammonium, Dodecyltrimethylammonium, Methyltrioctylammonium, Heptyltributylammonium, Tetrapropylammonium, Tetrapentylammonium, Tetrahexylammonium, Tetraheptylammonium, Tetraoctylammonium, Tetradecylammonium, Butyltripropylammonium, Methyltributylammonium, Pentyltributylammonium, Methyldiethylpropylammonium, Ethyldimethylpropylammonium, Tetradodecylammonium, Tetraoctadecylammonium, Hexadecyltrimethylammonium, Benzyltrimethylammonium, Benzyldimethylpropylammonium, Benzyldimethyloctylammonium, Benzyltributylammonium, Benzyltriethylammonium, Phenyltrimethylammonium, Benzyldimethyltetradecylammonium, Benzyldimethylhexadecylammonium, Dimethyldiphenylammonium, Methyltriphenylammonium, But-2-enyltriethylammonium, N,N-Dimethyltetramethyleneammonium, N,N-Diethyltetramethyleneammonium, Tetramethylphosphonium, Tetrabutylphosphonium, Ethyltrimethylphosphonium, Trimethylpentylphosphonium, Octyltrimethylphosphonim, Dodecyltrimethylphosphonium, Trimethylphenylphosphonium, Diethyldimethylphosphonium, Dicyclohexyldimethylphosphonium, Dimethyldiphenylphosphonium, Cyclohexyltrimethylphosphonium, Triethylmethylphosphonium, Methyltri(isopropyl)phosphonium, Methyltri(n-propyl)phosphonium, Methyltri(n-butyl)phosphonium, Methyltri(2-methylpropyl)phosphonium, Methyltricyclohexylphosphonium, Methyltriphenylphosphonium, Methyltribenzylphosphonium, Methyltri(4-methylphenyl)phosphonium, Methyltrixylylphosphonium, Diethylmethylphenylphosphonium, Dibenzylmethylphenylphosphonium, Ethyltriphenylphosphonium, Tetraethylphosphonium, Ethyltri(n-propyl)phosphonium, Triethylpentylphosphonium, Hexadecyltributylphosphonium, Ethyltriphenylphosphonium, n-Butyltri(n-propyl)phosphonium, Butyltriphenylphosphonium, Benzyltriphenylphosphonium, (β-Phenylethyl)dimethylphenylphosphonium, Tetraphenylphosphonium, Triphenyl(4-methylphenyl)phosphonium, Tetrakis(hydroxymethyl)phosphonium, Tetrakis(2-hydroxyethyl)phosphonium.

The following cations are exemplary of those of formula II: N-Methylpyridinium, N-Ethylpyridinium, N-Hexadecylpyridinium, N-Methylpicolinium.

The following cations are exemplary of those of formula III: 1,2-Bis(trimethylammonium)ethane, 1,3-Bis(trimethylammonium)propane, 1,4-Bis(trimethylammonium)butane, 1,3-Bis(trimethylammonium)butane.

The following cations are exemplary of those of formula IV: Bis(triphenylphosphine)iminium, Bis(tritolylphosphine)iminium.

And the following cations are exemplary of those of formula V: 1-Methyl-3-methylimidazolium, 1-Methyl-3-ethylimidazolium, 1-Methyl-3-n-propylimidazolium, 1-Methyl-3-n-butylimidazolium, 1-Methyl-3-benzylimidazolium, 1-Methyl-2-methyl-3-ethylbenzimidazolium.

Advantageously, onium cations corresponding to the above formula (I) are used in which A is phosphorus, and $R_1$, $R_2$, $R_3$ and $R_4$, which may be identical or different, are each a linear or branched alkyl radical having from 1 to 8 carbon atoms, a phenyl or 4-methylphenyl radical.

A tetralkylphosphonium chloride is preferably used.

Tetrabutylphosphonium chloride, commercially available and particularly efficient, is more especially preferred.

It will be appreciated that certain palladium compounds such as $PBu_4PdCl_3$ may constitute both a source of palladium and a means for introducing at least a fraction of the quaternary onium chloride in the sense described above.

As indicated above, the process according to the present invention may be carried out using an alkali metal or alkaline earth metal compound as an ionic chloride. Exemplary such chlorides are LiCl and $CaCl_2$, with LiCl being the preferred.

It is of course possible to use a mixture of inorganic chlorides and/or of quaternary onium chlorides.

In general, the amount of ionic chloride to be employed in the reaction mixture will be such that the $Cl^-/Pd$ molar ratio is greater than or equal to 1, this ratio having no upper limits other than by reason of economic constraints and/or difficulties of handling of the reaction mixture.

Said molar ratio preferably ranges from 3 to 100.

The reaction mixture may, if appropriate, contain an organic diluent or solvent. When it is desired to carry out the reaction in the presence of a diluent or solvent, polar, aprotic, basic or nonbasic solvents are used. Nitriles such as acetonitrile are exemplary aprotic, nonbasic polar solvents which are suitable for the process of the invention.

When only alkali or alkaline earth metal chlorides are used, it is advantageous to conduct the reaction in a polar, aprotic and preferably basic solvent.

By "aprotic and basic polar solvent" are intended compounds of formula (VI):

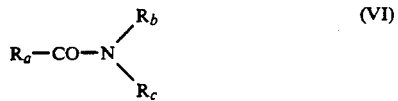

in which $R_a$, $R_b$ and $R_c$, which may be identical or different, are each an alkyl radical, a cycloalkyl radical, an aralkyl radical or a monocyclic aryl radical having up to 10 carbon atoms, with the proviso that two of the radicals $R_a$, $R_b$ or $R_c$ may together form a single divalent radical —$(CH_2)_y$—, wherein y is an integer ranging from 3 to 12, and with the further proviso that $R_a$ may also be a radical

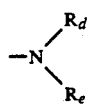

in which $R_d$ and $R_e$, which may be identical or different, are each an alkyl radical having up to 4 carbon atoms.

Exemplary such solvents include tetramethylurea, N,N-dimethylacetamide, N,N-diethylacetamide, N,N-dicyclohexylacetamide, N,N-dimethylpropionamide, N,N-diethylpropionamide, N,N-diethyl-n-butyramide, N,N-dimethylbenzamide, N,N-dicyclohexylbenzamide, N,N-diethyl-m-toluamide, N-acetylpyrrolidine, N-acetylpiperidine, N-(n-butyryl)piperidine, N-methyl-2-pyrrolidone, N-ethyl-2-pyrrolidone, N-methyl-2-piperidone and N-methyl-epsiloncaprolactam.

N-Methyl-2-pyrrolidone is particularly suitable for carrying out the process of the invention.

When a solvent is used, the amount thereof is at least 10% by volume of the reaction mixture; good results are obtained when on the order of 20% to 90% by volume of solvent is employed.

It is generally possible to conduct the reaction in liquid phase at a temperature ranging from 50° to 180° C., preferably from 80° to 150°, under a carbon monoxide pressure which is greater than or equal to 20 bar and preferably less than or equal to 250 bar.

Preferably, the carbon monoxide pressure will range from 90 to 180 bar.

Inert gases such as nitrogen, argon or carbon dioxide may be present in addition to the carbon monoxide.

Upon completion of the reaction or of the time permitted for the reaction, the desired diester is recovered by any suitable means, for example by extraction and/or distillation.

In order to further illustrate the present invention and the advantages thereof, the following specific examples are given, it being understood that same are intended only as illustrative and in nowise limitative.

EXAMPLES 1 to 5: Control Tests (a) to (d)

The following materials were introduced into a 20-cm³ stainless steel (Hastelloy B2) autoclave, purged with argon beforehand:

(i) 8.7 mmol of 1,2-dimethoxy-3-butene;

(ii) 1.66 mg-at. of palladium in the form of $PdCl_2$;

(iii) 6 mmol of ionic chloride; and (iv) if appropriate, 10 cm³ of solvent.

The autoclave was closed hermetically, placed in an agitating oven and connected to the pressurized gas supply. The reactor was purged cold with carbon monoxide and heated to 95° C. The pressure was then adjusted to 140 bar. After the reaction, the autoclave was cooled and degassed.

The reaction mixture was then analyzed by gas phase chromatography.

The particular reaction conditions and the results obtained are reported in Table I below, in which t denotes the reaction period at temperature, HD (%) denotes the molar quantity of methyl 3-hexenedioate formed per 100 moles of 1,2-dimethoxy-3-butene charged, and DC (%) denotes the degree of conversion of 1,2-dimethoxy-3-butene.

TABLE I

| Example | Ionic chloride | Solvent | t (h) | DC (%) | 3HD (%) |
|---|---|---|---|---|---|
| 1 | PBu4Cl | none | 6 | 100 | 80 |
| 2 | PBu4Cl | NMP | 6 | 100 | 92.5 |
| 3 | LiCl | NMP | 6 | 100 | 86 |
| 4 | NMe4Cl | NMP | 6 | 100 | 82 |
| 5 | DMICl | NMP | 6 | 100 | 91 |
| a | none | ethanol | 6 | 100 | 3 |
| b | none | acetonitrile | 6 | 37 | 8 |
| c | none | NMP | 6 | 57 | 9 |
| d | none | p-DCB | 6 | 100 | 38 |

DMI Cl = N,N-dimethylimidazolium chloride
NMP = N-methyl-2-pyrrolidone
p-DCB = para-dichlorobenzene

EXAMPLES 6 AND 7

The following materials were introduced into a 125-cm$^3$ stainless steel (Hastelloy B2) autoclave, purged with argon beforehand:

(i) 25 mmol of 1,2-dimethoxy-3-butene;
(ii) 5 mmol of palladium in the form of PdCl$_2$;
(iii) tetrabutylphosphonium chloride; and
(iv) if appropriate, 30 cm$^3$ of solvent.

The autoclave was then closed and the procedure described in Examples 1 to 5 was repeated (t=95° C.; p=140 bar).

The particular reaction conditions and the results obtained are reported in Table II below:

TABLE II

| Example | PBu$_4$Cl mmol | Solvent | t (h) | DC (%) | 3HD (%) |
|---|---|---|---|---|---|
| 6 | 5 | acetonitrile | 8 | 96 | 72 |
| 7 | 27 | none | 8 | 99 | 80 |

EXAMPLES 8 and 9

The procedure of Example 7 was repeated in the autoclave according to the above technique, on a charge modified as follows:

(i) a mixture of 1,4-dimethoxy-2-butene (1,4-DMB) and of 1,2-dimethoxy-3-butene (1,2-DMB) was introduced,
(ii) 19 mmol of PBu$_4$Cl were introduced.

The particular reaction conditions and the results obtained are reported in Table III below:

TABLE III

| Example | 1,4-DMB mmol | 1,2-DMB mmol | t (h) | 3HD (%) |
|---|---|---|---|---|
| 8 | 18.5 | 8 | 4.8 | 65 |
| 9 | 8 | 17.5 | 5.7 | 74 |

In these two tests, the conversion of the dimethoxybutenes was complete.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a diester of a hexene-1,6-dioic acid, comprising reacting at least one 1,2-dialkoxy-3-butene with carbon monoxide in the presence of a catalytically effective amount of a palladium-based catalyst and a halogen compound, in liquid phase, at elevated temperature and at superatmospheric pressure.

2. The process as defined by claim 1, wherein one of said at least one 1,2-dialkoxy-3-butene is 1,2-dimethoxy-3-butene.

3. The process as defined by claim 1, wherein one of said at least one 1,2-dialkoxy-3-butene is 1,2-diethoxy-3-butene.

4. The process as defined by claim 1, said at least one 1,2-dialkoxy-3-butene comprising an admixture thereof with a 1,4-dialkoxy-2-butene.

5. The process as defined by claim 1, said halogen compound comprising an ionic chloride, the cation of which being selected from among:
(a) an alkali metal cation,
(b) an alkaline earth metal cation, and
(c) a quaternary onium cation of one of the Group VB elements nitrogen and phosphorus, such element being tetracoordinated to carbon atoms, with the proviso that the nitrogen may be coordinated to two pentavalent phosphorus atoms.

6. The process as defined by claim 5, said halogen compound comprising a quaternary onium chloride of one of the Group VB elements nitrogen and phosphorus, such element being tetracoordinated to carbon atoms, with the proviso that the nitrogen may be coordinated to two pentavalent phosphorus atoms.

7. The process as defined by claim 6, said quaternary onium cation having one of the following formulae (I) to (V):

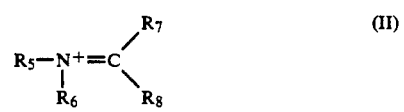

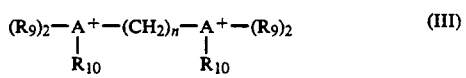

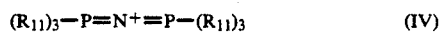

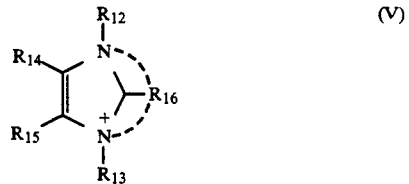

in which A is a nitrogen or phosphorus atom; R$_1$, R$_2$, R$_3$, R$_4$, which may be identical or different, are each a linear or branched having from 1 to 16 carbon atoms, unsubstituted or substituted by a phenyl, hydroxyl, halo, nitro, alkoxy or alkoxycarbonyl group, a linear or branched alkenyl radical having from 2 to 12 carbon atoms, an aryl radical having from 6 to 10 carbon atoms, unsubstituted or substituted by one or more alkyl radicals having from 1 to 4 carbon atoms, alkoxy, alkoxycarbonyl or halo radicals, with the proviso that two of said radicals R$_1$ to R$_4$ may together form a linear or branched alkylene, alkenylene or alkadienylene radical having from 3 to 6 carbon atoms; R$_5$, R$_6$, R$_7$, R$_8$, which may be identical or different, are each a linear or branched alkyl radical having from 1 to 4 carbon atoms, with the proviso that the radicals R$_7$ and R$_8$ may together form an alkylene radical having from 3 to 6 carbon atoms, and with the further proviso that the radicals R$_6$ and R$_7$ or R$_8$ may together form an alkylene, alkylene or alkadienylene radical having 4 carbon atoms and constituting a nitrogenous heterocyclic ring with N; R$_9$ is a linear or branched alkyl radical having from 1 to 4 carbon atoms or a phenyl radical; R$_{10}$ is a linear or branched alkyl radical having from 1 to 4 carbon atoms, the same as or different from R$_9$, a linear or branched alkenyl radical having from 2 to 12 carbon atoms; n is an integer greater than or equal to 1 and less than or equal to 10; $R_{11}$ is an aryl radical having from 6 to 10 carbon atoms, unsubstituted or substituted by one or more alkyl groups having from 1 to 4 carbons, alkoxy, alkoxycarbonyl or halo groups, $R_{12}$ and $R_{13}$, which may be identical or different, have the definitions given above for $R_1$ to $R_4$; and $R_{14}$ to $R_{16}$, which may be identical or different, are each a hydrogen atom, a linear or branched radical having from 1 to 16 carbon atoms, unsubstituted or substituted or by a phenyl, hydroxyl, halo, nitro, alkoxy or alkoxycarbonyl group, a linear or branched alkenyl radical having from 2 to 12 carbon atoms, an aryl radical having from 6 to 10 carbon atoms, unsubstituted or substituted by one or more alkyl radicals having from 1 to 4 carbon atoms, alkoxy, alkoxycarbonyl or halo radicals, with the proviso that the radicals $R_{14}$ and $R_{15}$ may together form a linear or branched alkylene, alkenylene or alkadienylene radical having from 3 to 6 carbon atoms, to constitute an aromatic ring with the two adjoining carbon atoms of the imidazole ring.

8. The process as defined by claim 7, said quaternary onium cation having the formula (I) in which A is phosphorus, and $R_1$, $R_2$, $R_3$ and $R_4$, which may be identical or different, are each a linear or branched alkyl radical having from 1 to 8 carbon atoms, a phenyl or 4-methylphenyl radical.

9. The process as defined by claim 1, said halogen compound comprising tetrabutylphosphonium chloride.

10. The process as defined by claim 1, said halogen compound comprising an alkali or alkaline earth metal chloride.

11. The process as defined by claim 1, said halogen compound comprising lithium chloride.

12. The process as defined by claim 10, carried out in an aprotic and basic polar solvent.

13. The process as defined by claim 12, said solvent having the formula (VI):

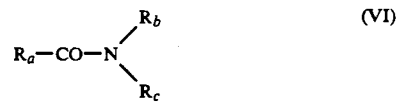

in which $R_a$, $R_b$ and $R_c$, which may be identical or different, are each an alkyl radical, a cycoalkyl radical, an aralkyl radical or a monocyclic aryl radical having up to 10 carbon atoms, with the proviso that two of the radicals $R_a$, $R_b$ or $R_c$ or may together form a single divalent radical $(CH_2)_y$, wherein y is an integer ranging from 2 to 12, and with the further proviso that $R_a$ may be a radical:

in which $R_d$ and $R_e$, which may be identical or different, are each an alkyl radical having up to 4 carbon atoms.

14. The process as defined by claim 12, said solvent comprising at least 10% by volume of the reaction mixture.

15. The process as defined by claim 12, said solvent comprising N-methyl-2-pyrrolidone.

16. The process as defined by claim 5, the molar ratio of chloride anion to palladium ranging from 3 to 100.

17. The process as defined by claim 1, the concentration of palladium in the reaction mixture ranging from $10^{-3}$ to 1 mol/l.

18. The process as defined by claim 1, carried out at a temperature ranging from 50° to 180° C.

19. The process as defined by claim 1, carried out under a pressure greater than or equal to 20 bar and less than or equal to 250 bar.

20. The process as defined by claim 19, carried out under a pressure ranging from 90 to 180 bar.

21. The process as defined by claim 1, said palladium-based catalyst comprising palladium chloride.

* * * * *